United States Patent
Inoue

(10) Patent No.: US 10,441,233 B2
(45) Date of Patent: Oct. 15, 2019

(54) IMAGING CONTROL APPARATUS, X-RAY IMAGING APPARATUS, IMAGING CONTROL METHOD, AND STORAGE MEDIUM

(71) Applicant: CANON KABUSHIKI KAISHA, Tokyo (JP)

(72) Inventor: Noboru Inoue, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 527 days.

(21) Appl. No.: 15/130,113

(22) Filed: Apr. 15, 2016

(65) Prior Publication Data

US 2016/0228081 A1    Aug. 11, 2016

Related U.S. Application Data

(63) Continuation of application No. PCT/JP2014/004976, filed on Sep. 29, 2014.

(30) Foreign Application Priority Data

Oct. 30, 2013    (JP) .................................. 2013-225822

(51) Int. Cl.
*A61B 6/00*    (2006.01)

(52) U.S. Cl.
CPC ................ *A61B 6/465* (2013.01); *A61B 6/54* (2013.01); *A61B 6/5241* (2013.01); *A61B 6/563* (2013.01)

(58) Field of Classification Search
CPC ... A61B 6/4233; A61B 6/4266; A61B 6/4283; A61B 6/4291; A61B 6/4405; A61B 6/4494; A61B 6/463; A61B 6/464; A61B 6/465; A61B 6/488; A61B 6/5294; A61B 6/542; A61B 6/545; A61B 6/548; A61B 6/563; A61B 6/585; A61B 6/587;
(Continued)

(56) References Cited

U.S. PATENT DOCUMENTS

| 2003/0142859 A1 | 7/2003 | Okuzawa ...................... 382/132 |
| 2005/0078940 A1 | 4/2005 | Wakita et al. ................ 386/231 |
| 2011/0038738 A1 | 2/2011 | Ando et al. ................... 348/162 |

(Continued)

FOREIGN PATENT DOCUMENTS

| JP | H10-155745 | 6/1998 |
| JP | H11-009580 | 1/1999 |

(Continued)

OTHER PUBLICATIONS

Translation of JP 2008-173886. (Year: 2008).*
(Continued)

*Primary Examiner* — Chih-Cheng Kao
(74) *Attorney, Agent, or Firm* — Venable LLP

(57) ABSTRACT

An imaging control apparatus for an X-ray imaging apparatus which performs X-ray imaging in accordance with a plurality of pieces of imaging information displayed in an information display area of a display unit includes a display control unit which controls the display position of prepared imaging information in the completed state of preparation for X-ray imaging and the display position of unprepared imaging information in the uncompleted state of preparation for X-ray imaging in accordance with a reference position set in the information display area.

24 Claims, 10 Drawing Sheets

(58) Field of Classification Search
CPC ...... G03B 42/02; G03B 42/025; G03B 42/04; G06F 19/3481; G16H 20/40
See application file for complete search history.

(56) References Cited

U.S. PATENT DOCUMENTS

| | | | | |
|---|---|---|---|---|
| 2014/0112447 A1* | 4/2014 | Semba | ............... | A61B 6/5241 |
| | | | | 378/98 |
| 2014/0119514 A1* | 5/2014 | Miyazawa | ............ | A61B 6/463 |
| | | | | 378/98 |
| 2016/0128649 A1* | 5/2016 | Miyazawa | ............ | A61B 6/025 |
| | | | | 378/21 |
| 2016/0213347 A1* | 7/2016 | Kawanishi | ........... | A61B 6/4464 |
| 2017/0163869 A1* | 6/2017 | Semba | ............... | A61B 6/465 |

FOREIGN PATENT DOCUMENTS

| | | |
|---|---|---|
| JP | 2000-166908 | 6/2000 |
| JP | 2003-284709 | 10/2003 |
| JP | 2003-290188 | 10/2003 |
| JP | 2005-092464 | 4/2005 |
| JP | 2008-173886 | 7/2008 |
| JP | 2012-155779 | 8/2012 |
| WO | WO 2011/142157 A | 11/2011 |

OTHER PUBLICATIONS

Translation of JP 2012-155779. (Year: 2012).*
Translation of JP 2005-092464. (Year: 2005).*
"Digital Radiography", General Catalog CXDI Canon (http://www.canon-lcs.co.jp/service/pdf-catalog/pdf/cxdi-all.pdf) (Dec. 2013).

* cited by examiner

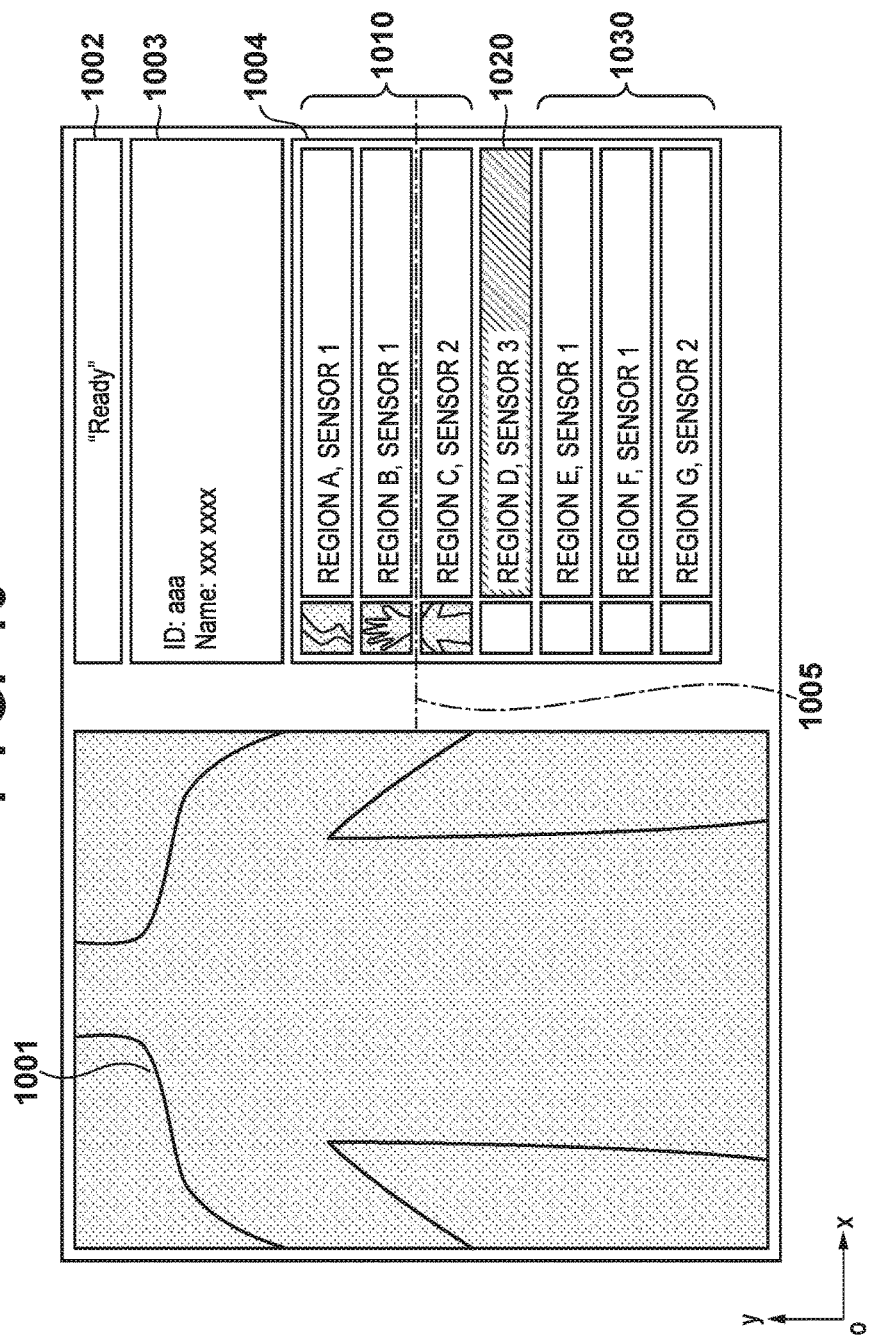

IMAGING CONTROL APPARATUS, X-RAY IMAGING APPARATUS, IMAGING CONTROL METHOD, AND STORAGE MEDIUM

This application is a continuation of International Patent Application No. PCT/JP2014/004976 filed on Sep. 29, 2014, and claims priority to Japanese Patent Application No. 2013-225822 filed on Oct. 30, 2013, the entire content of both of which is incorporated herein by reference.

TECHNICAL FIELD

The present invention relates to an imaging control apparatus, an X-ray imaging apparatus, an imaging control method, and a storage medium.

BACKGROUND ART

In recent years, there has been popularity in diagnoses and inspections based on imaging using radiation (for example, X-rays). Such an inspection or the like proceeds based on an inspection order including a plurality of pieces of imaging information. Imaging information in this case is information indicating imaging conditions including an imaging region, an imaging method, and image processing which are required by a doctor. For example, a radiation technician or the like manually sets such information in accordance with an inspection order.

Online systematization using an HIS (Hospital Information System), RIS (Radiology Information System), and the like is underway in hospitals. This makes it possible to transfer an inspection order generated outside a hospital in advance to a radiation imaging apparatus connected via a network and to proceed with an inspection. In this case, when an imaging technician selects imaging information of the inspection order displayed on the display unit of the radiation imaging apparatus, parameters are set in accordance with the imaging information. The technician then can perform imaging using the set parameters.

In general, a plurality of pieces of imaging information are registered in accordance with an inspection order. The display unit of the radiation imaging apparatus includes a display portion on which a plurality of pieces of imaging information can be displayed and a display portion on which obtained images, image processing parameters, and the like are displayed. For this reason, a protocol display portion on which an imaging protocol is displayed cannot help being reduced. This can lead to a failure to display all the imaging protocol of the inspection order. In this case, the radiation technician needs to perform imaging while checking a protocol for the next imaging operation by scrolling the display on the protocol display portion.

The radiation imaging apparatus disclosed in NPL 1 is designed to automatically display, on a display unit, after imaging, imaging information indicating the completed state (Ready) of an imaging preparation as imaging information for the execution of the next imaging operation.

CITATION LIST

Non Patent Literature

NPL 1: Digital Radiography General Catalog CXDI Canon (http://www.canon-lcs.co.jp/service/pdf-catalog/pdf/cxdi-all.pdf)

SUMMARY OF INVENTION

Technical Problem

However, it is only imaging information in a completed state of an imaging preparation that is automatically displayed. Thereafter, no display control is performed concerning the display of pre-imaging imaging information to be used for imaging. For this reason, a radiation technician needs to check the display unit every time performing imaging. That is, the technician needs to manually perform the operation of checking the presence/absence of pre-imaging imaging information of imaging information corresponding to an inspection order by scrolling the display on the display unit.

In consideration of the situation of the related art described above, the present invention provides a technique capable of allowing an easy check on imaging information corresponding to an inspection order in accordance with the progress of X-ray imaging.

Solution to Problem

An imaging control apparatus according to one aspect of the present invention is an imaging control apparatus for an X-ray imaging apparatus which performs X-ray imaging in accordance with a plurality of pieces of imaging information displayed in an information display area of a display unit, comprising a display control unit configured to control a display position of prepared imaging information in a completed state of preparation for X-ray imaging and a display position of unprepared imaging information in an uncompleted state of preparation for X-ray imaging in accordance with a reference position set in the information display area.

Advantageous Effects of Invention

According to the present invention, it is possible to allow an easy check on imaging information corresponding to an inspection order in accordance with the progress of X-ray imaging.

Further features of the present invention will become apparent from the following description of exemplary embodiments (with reference to the attached drawings).

BRIEF DESCRIPTION OF DRAWINGS

The accompanying drawings, which are incorporated in and constitute a part of the specification, illustrate embodiments of the invention and, together with the description, serve to explain the principles of the invention.

FIG. 10 is a view exemplarily showing the screen of a display unit.

DESCRIPTION OF EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

Figure 1:
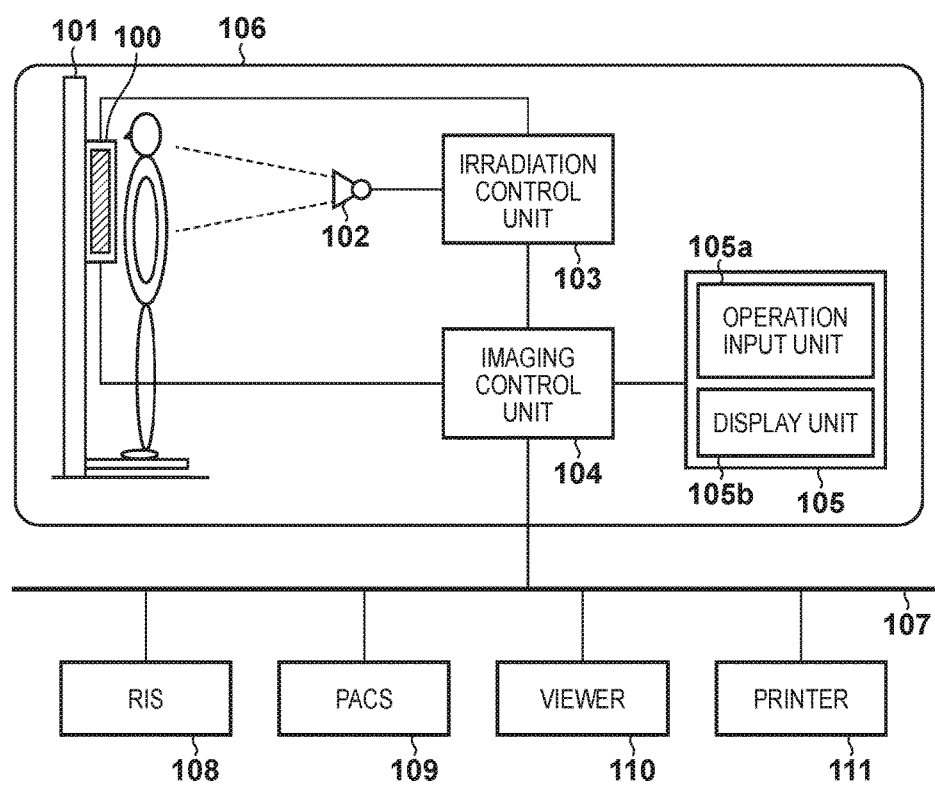
FIG. 1 is a view exemplarily showing the functional arrangement of an X-ray imaging apparatus according to an embodiment.

FIG. 1 is a view exemplarily showing the functional arrangement of an X-ray imaging apparatus 106 according to the first embodiment. The X-ray imaging apparatus 106 of an X-ray imaging system can be connected to an RIS (Radiology Information System) 108 via a network 107. The X-ray imaging system includes a PACS 109 which archives and manages X-ray images obtained by the X-ray imaging apparatus 106, a viewer 110 which displays diagnosis X-ray images, and a printer 111. The RIS (Radiology Information System) 108, the X-ray imaging apparatus 106, the PACS 109, and the viewer 110 are connected to each other via the network 107.

The X-ray imaging apparatus 106 includes a sensor unit 101, an X-ray generation unit 102, an irradiation control unit 103, an imaging control unit 104, and an operation display unit 105. The X-ray generation unit 102 includes, for example, an X-ray tube, and performs irradiation with X-rays under the control of the irradiation control unit 103. The irradiation control unit 103 controls irradiation with X-rays by the X-ray generation unit 102. The sensor unit 101 includes a sensor 100 which detects X-rays emitted from the X-ray generation unit 102. The imaging control unit 104 controls X-ray imaging by the X-ray imaging apparatus 106.

The operation display unit 105 includes an operation input unit 105a of the X-ray imaging apparatus 106 and a display unit 105b of the X-ray imaging apparatus 106. The display unit 105b displays imaging information and obtained images. In addition, the operation input unit 105a is used to select imaging information, perform an operation in image processing, and issue an instruction to proceed with imaging. Furthermore, the input operation of the operation input unit 105a includes an input operation from an external device such as a magnetic card or barcode reader. The operation display unit 105 may have an arrangement independent of the imaging control unit 104 or may be provided as an arrangement inside the imaging control unit 104.

The imaging control unit 104 performs display control to display, on the display unit 105b, an inspection order received from the RIS 108 or imaging information of an inspection order input by an imaging technician with the operation input unit 105a. In addition, the imaging control unit 104 transmits imaging conditions such as a tube current, a tube voltage, and an irradiation time to the irradiation control unit 103 in accordance with imaging information selected from a plurality of pieces of imaging information associated with an inspection order. The irradiation control unit 103 applies a high voltage to the X-ray generation unit 102 to generate X-rays in accordance with imaging conditions upon the pressing of an irradiation button via the operation input unit 105a.

The sensor unit 101 functioning as an X-ray detection unit A/D-converts charge corresponding to the amount of X-rays transmitted through an object detected by the sensor 100, and transmits an X-ray digital image having undergone A/D conversion to the imaging control unit 104. The imaging control unit 104 performs various types of correction processing and image processing for the received X-ray digital image based on image processing parameters associated with the imaging information selected by the imaging technician. The X-ray digital image having undergone the image processing is archived in the PACS 109 and output to the viewer 110 or the printer 111, thereby performing a diagnosis.

Note that the arrangement of the X-ray imaging apparatus 106 is sometimes called an X-ray imaging system. In addition, the irradiation control unit 103 as a component of the X-ray imaging system can also function as an irradiation control apparatus which controls the X-ray generation unit 102. The imaging control unit 104 as a component of the X-ray imaging system can also function as an imaging control apparatus which controls X-ray imaging.

Figure 2:
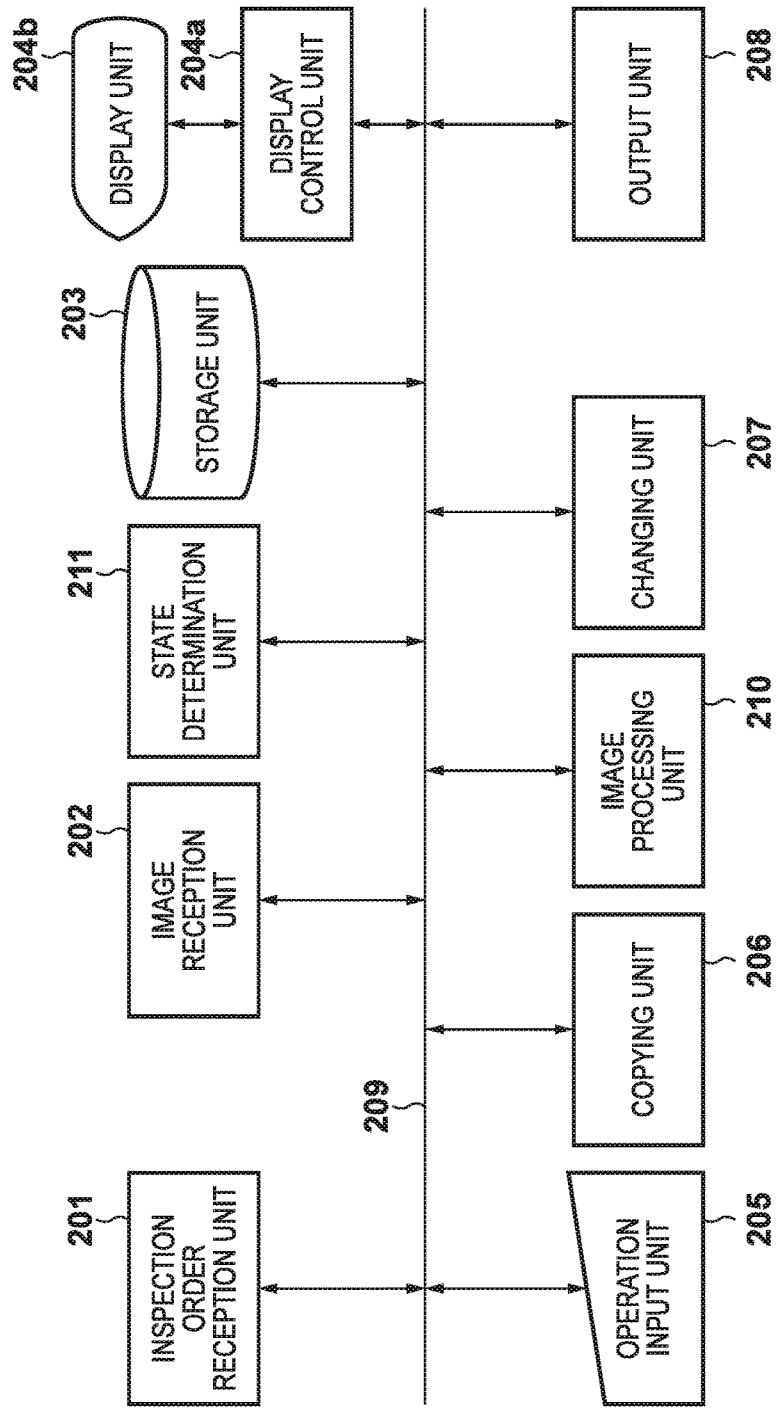
FIG. 2 is block diagram showing the arrangement of an imaging control unit.

FIG. 2 is a block diagram showing the arrangement of the imaging control unit 104. FIG. 1 shows an arrangement in which the operation input unit 105a and the display unit 105b are provided outside the imaging control unit 104. However, these components may be provided in the imaging control unit 104. An inspection order reception unit 201 receives an inspection order input from the RIS 108 or the operation input unit. An inspection order is constituted by patient information concerning a patient to be imaged and imaging information indicating imaging contents. In this case, imaging information is information indicating imaging conditions including information concerning an imaging region, imaging method, and image processing which are required by the doctor.

An image reception unit 202 receives an X-ray digital image obtained by the X-ray imaging apparatus 106 from the sensor unit 101. Note that an image to be received is sometimes input via the network 107 or input via a storage medium such as a CD-ROM or DVD.

A storage unit 203 stores imaging information obtained upon imaging (post-imaging imaging information). In addition, an image input from the image reception unit 202 is stored in the storage unit 203 in association with the imaging information of an inspection order.

The operation detection unit 211 receives pieces of state information indicating states of preparation for imaging from the sensor unit 101 and the irradiation control unit 103, and determines whether an imaging preparation is complete.

A display control unit 204a performs display control for the display of an X-ray digital image and imaging information on a display device (display unit 204b) such as a CRT or liquid crystal monitor.

FIG. 10 is a view exemplarily showing the screen of the display unit 204b (display unit 105b). The screen displayed on the display unit 204b (display unit 105b) includes an image display area 1001, a state display area 1002, a patient information display area 1003, and an imaging information display area 1004. Note that an illustration of a scroll bar 320 in the imaging information display area 1004 in FIG. 10 is omitted for the sake of simplification and facilitation of information on the drawing.

An image obtained by X-ray imaging is previewed in the image display area 1001. The display control unit 204a can display patient information, imaging information, X-ray irradiation conditions, and the like in the form of annotation in accordance with settings.

A state determination unit 211 receives state information indicating a state of preparation for imaging from the sensor unit 101 and the irradiation control unit 103, and determines, based on the combination of pieces of state information, whether the preparation for imaging is complete. The display control unit 204a switches the display in the state display area 1002 in accordance with this determination result.

Assume that state information from the irradiation control unit 103 indicates an uncompleted state of preparation for X-ray irradiation, or state information from the sensor unit 101 indicates the uncompleted state of preparation for X-ray detection. In this case, the state determination unit 211 determines that the imaging preparation is not complete. In accordance with this determination result, the display control unit 204a displays, in the state display area 1002, "Not Ready" as an indication indicating that the imaging preparation is not complete.

Assume that state information from the irradiation control unit 103 indicates a completed state of preparation for X-ray irradiation, or state information from the sensor unit 101 indicates the completed state of preparation for X-ray detection. In this case, the state determination unit 211 determines that the imaging preparation is complete. In accordance with this determination result, the display control unit 204a displays, in the state display area 1002, "Ready" as an indication indicating that the imaging preparation is complete (FIG. 10).

The patient information display area 1003 is an area in which patient information such as a patient ID and a patient name is displayed. A plurality of pieces of imaging information corresponding to an inspection order are displayed side by side in the imaging information display area 1004 (to be also simply referred to as a display area hereinafter). The display of imaging information includes the display of an imaging name, sensor type, and the like. When using a single sensor, one sensor is displayed. When using a plurality of sensors, a plurality of sensors (for example, sensors 1, 2, 3, . . . ) are displayed. In addition, with regard to post-imaging imaging information having undergone X-ray imaging, a reduced image (thumbnail image) obtained as reduced display of an obtained image is displayed.

Imaging information 1010 indicates post-imaging information. Imaging information 1020 indicates pre-imaging imaging information in the completed state of preparation for imaging (prepared imaging information). The imaging information 1020 corresponds to imaging information 302 in FIG. 3, imaging information 502 in FIG. 5, imaging information 702 in FIG. 7, imaging information 802 in FIG. 8, and imaging information 902 in FIG. 9. Imaging information 1030 indicates pre-imaging imaging information in the uncompleted state of preparation for imaging (unprepared imaging information).

When the state of imaging preparation has changed from the uncompleted state (Not ready) to the completed state (Ready: FIG. 10), the display control unit 204a completes a preparation for X-ray imaging in the display of the imaging information display area 1004. The display control unit 204a then compares the display position of the imaging information 1020 to be used for X-ray imaging next with a reference position 1005 of the information display area. In accordance with this comparison result, the display control unit 204a controls the display of the imaging information 1020 and the imaging information 1030 in the uncompleted state of preparation for X-ray imaging.

For example, the display control unit 204a changes the display positions of the imaging information 1020 (prepared imaging information) and the imaging information 1030 (unprepared imaging information) so as to match the display of the imaging information 1020 (prepared imaging information) with the reference position 1005. Alternatively, if no prepared imaging information is displayed in the information display area, the display control unit 204a changes the display positions of prepared imaging information and unprepared imaging information so as to display them in the information display area. At this time, the display control unit 204a performs display control so as to also display post-imaging imaging information stored in the storage unit 203 on the display unit 204b. The detailed contents of display control by the display control unit 204a will be described later with reference to FIGS. 3 to 9.

An operation input unit 205 includes, for example, a mouse and a keyboard, and is used to select an inspection and issue an instruction to copy with respect to an image and an inspection order displayed on the display unit 204b. When, for example, adding and changing imaging information to perform imaging again, a copying unit 206 copies selected imaging information in response to an instruction to copy issued by the operation input unit 205. A changing unit 207 changes part of the imaging information copied by the copying unit 206. When the changing unit 207 has changed imaging information, output result information included in the imaging information before the change is cleared. An image processing unit 210 performs various types of correction processing and image processing for an X-ray digital image received from the sensor unit 101 based on image processing parameters associated with imaging information selected by an imaging technician. An output unit 208 outputs images and imaging information to the outside. The respective units in the imaging control unit 104 are connected to each other via a system bus 209.

Figure 3:
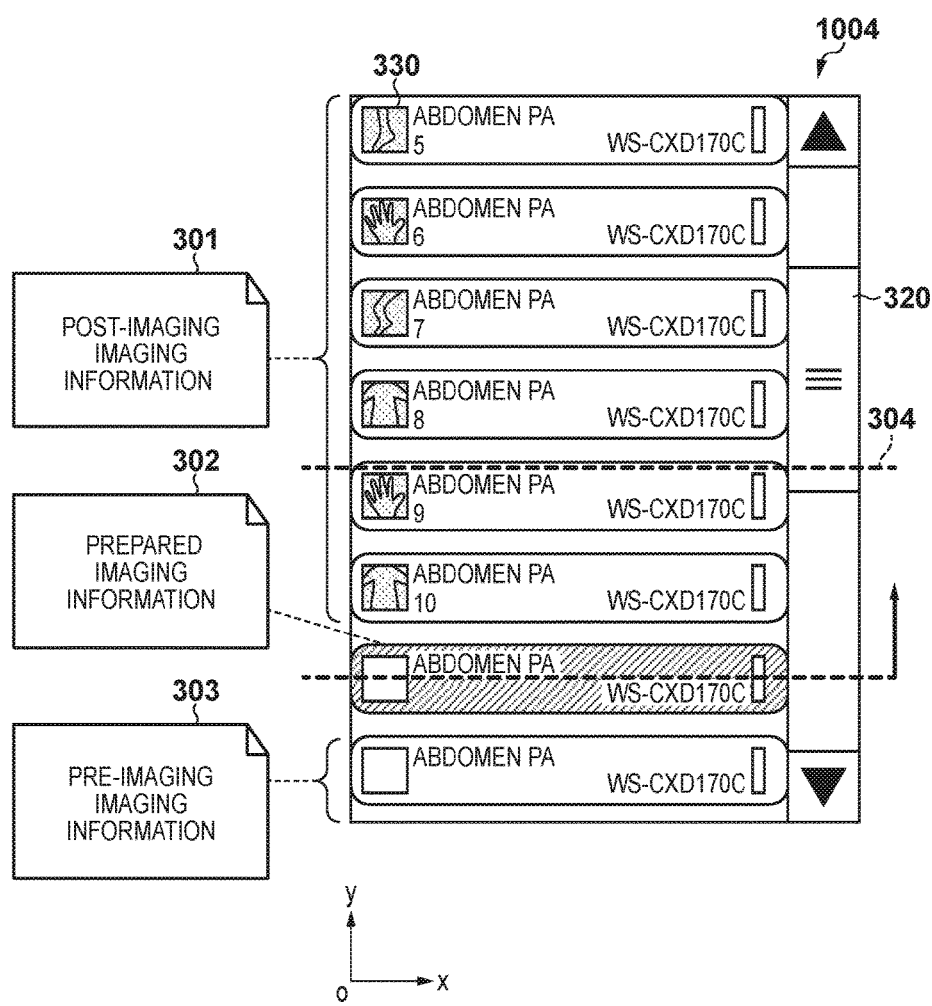
FIG. 3 is a view exemplarily showing display control performed by the display control unit.

FIG. 3 is a view exemplarily showing display in the imaging information display area 1004 on the display unit 204b described with reference to FIG. 2. If an inspection order includes a plurality of pieces of imaging information, the plurality of pieces of imaging information are displayed in the imaging information display area 1004.

Before the start of X-ray imaging, all the imaging information displayed in the imaging information display area 1004 is pre-imaging imaging information. When the operator vertically moves the scroll bar 320 via the operation input unit 205, the display control unit 204a performs display control so as to vertically move the display of the imaging information in the imaging information display area 1004. Note that display control of imaging information is not limited to the operation of the scroll bar 320. For example, the display control unit 204a can also perform display control of imaging information in accordance with the operation of a radiation technician (imaging technician) (for example, a swiping or flicking operation) of pressing a touch panel display with his/her finger and sliding the finger in a predetermined direction (for example, the upward direction or downward direction on the screen).

Imaging is sequentially executed with imaging information in the completed states of preparation for imaging with respect to the sensor unit 101 and the X-ray generation unit 102 in accordance with an imaging instruction issued by the imaging technician via the operation input unit 205. Imaging information obtained upon the execution of imaging is stored as post-imaging imaging information in the storage unit 203. In accordance with the progress of X-ray imaging, post-imaging imaging information and pre-imaging imaging information are displayed in the imaging information display area 1004. The display control unit 204a displays an image obtained by X-ray imaging in the image display area 1001, and also displays reduced display 330 (a thumbnail image) of the obtained image in the imaging information display area 1004 in combination with the display of imaging information. Such display control allows the technician to check pre-imaging imaging information in the completed state of preparation which is to be used for the next X-ray imaging operation while easily checking an obtained image.

In this case, the pre-imaging imaging information includes pre-imaging imaging information (prepared imaging information) in the completed state of preparation for imaging which can be used for the next imaging operation and pre-imaging imaging information (unprepared imaging information) in the uncompleted state of preparation for imaging with respect to the sensor unit.

In addition, the display control unit 204a performs display control so as to discriminate post-imaging imaging information, pre-imaging imaging information in the completed state of preparation for imaging, and pre-imaging imaging information in the uncompleted state of preparation for imaging. This display control can improve the visibility of each piece of imaging information. FIG. 3 exemplarily shows the respective pieces of imaging information in different types of hatchings. When performing identification display, it is possible to display a combination of changes in display color or different types of identification information and imaging information.

Referring to FIG. 3, imaging information 301 indicates post-imaging imaging information. If a plurality of pieces of post-imaging imaging information exist, a plurality of pieces of imaging information are displayed. The imaging information 302 indicates pre-imaging imaging information in the completed state of preparation for imaging (prepared imaging information). Since an imaging preparation is complete, the next imaging operation can be performed by using this imaging information. Imaging information 303 indicates pre-imaging imaging information in the uncompleted state of preparation for imaging (unprepared imaging information). The display of the unprepared imaging information 303 is changed into the display of prepared imaging information after the imaging information 302 is used for imaging and an imaging preparation is complete. The display control unit 204a performs display control so as to change the identification display with respect to the imaging information 303 in accordance with changes in the states of preparation for imaging by the sensor unit 101 and the X-ray generation unit 102. When the unprepared imaging information 303 is set in the completed state of preparation for imaging, the display is changed into the display of, for example, the imaging information 302. Assume that there are a plurality of pieces of pre-imaging imaging information 303 in the uncompleted state of preparation for imaging. In this case, the plurality of pieces of imaging information are displayed. In the case shown in FIG. 3, since there is a lack in the display space of the imaging information display area 1004, only one piece of imaging information is displayed.

The embodiment described below will exemplify a case in which the scrolling direction of the display of the imaging information display area 1004 is moved upward. However, the scope of the present invention is not limited to this, and display control can be performed so as to move the scrolling direction downward.

A reference position 304 indicates a position at which prepared imaging information is displayed in the imaging information display area 1004. In addition, post-imaging imaging information is displayed on the upper side of the reference position 304, and unprepared imaging information is displayed on the lower side of the reference position 304. That is, the reference position 304 is a boundary between post-imaging imaging information and unprepared imaging information. In the case shown in FIG. 3, the reference position 304 indicates the middle portion of the imaging information display area 1004 in the vertical direction. The reference position 304 is not limited to the middle portion of the imaging information display area 1004 in the vertical direction, and can be set with reference to an arbitrary position in the imaging information display area 1004. The display control unit 204a sets the reference position 304 via the operation input unit 205. In according to such setting, the display control unit 204a controls the display position of the reference position 304. The radiation technician (imaging technician) can set the reference position 304 by moving it in the imaging information display area 1004 via the operation input unit 205.

Referring to FIG. 3, the reference position 304 is set at the middle portion of the imaging information display portion, and the display control unit 204a performs display control so as to move the prepared imaging information 302 to the position of the reference position 304. The prepared imaging information 302 moves to the middle portion of the imaging information display portion and is displayed. In addition, post-imaging imaging information is displayed in the display area from the middle portion to the uppermost portion, and the unprepared imaging information 303 is displayed in the display area from the middle portion to the lowermost portion. This allows the radiation technician (imaging technician) to perform imaging while checking both the post-imaging imaging information 301 and the unprepared imaging information 303 planned to be used for imaging.

Figure 4:
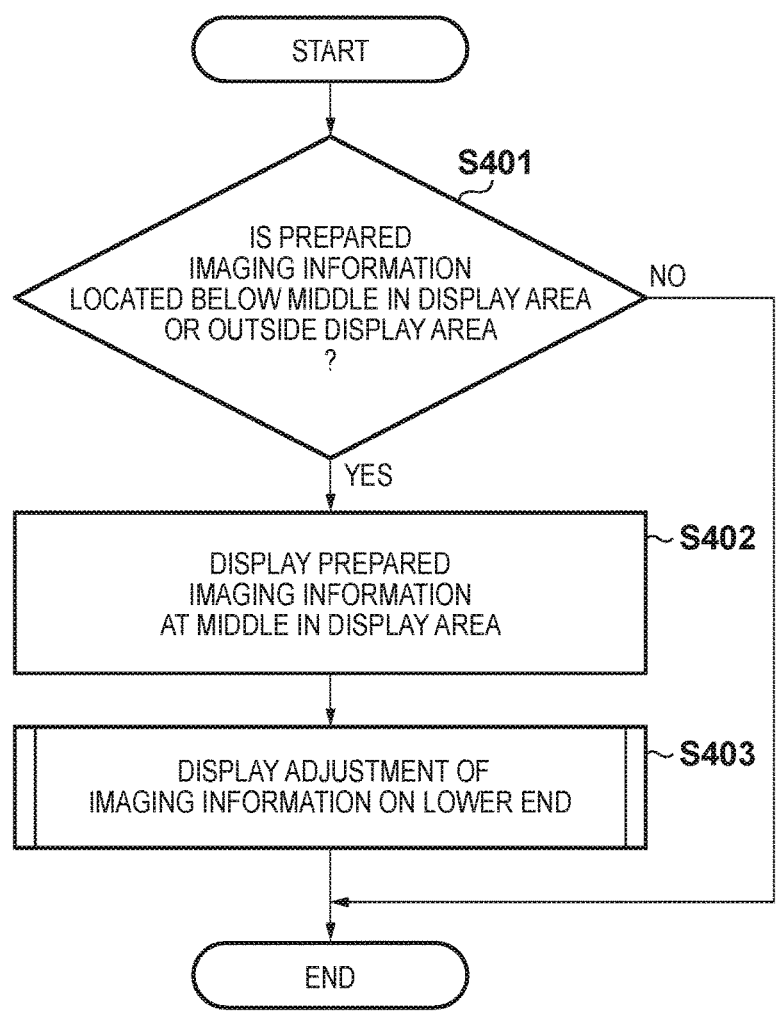
FIG. 4 is a flowchart for explaining a processing procedure by the display control unit.

FIG. 4 is a flowchart for explaining a processing procedure executed by the display control unit 204a concerning the display of imaging information (301, 302, and 303) shown in FIG. 3.

In step S401, the display control unit 204a determines the relative positional relationship between the display position of the prepared imaging information 302 and the reference position 304. If the display position of the imaging information 302 is located below the reference position 304 in the imaging information display area 1004, the process advances to step S402. Alternatively, if the display position of the imaging information 302 is located outside the imaging information display area 1004 (below the lower part of the imaging information display area) (YES in step S401), the process advances to step S402. If the display position of the imaging information 302 is located above the reference position 304 and the upper end of the display frame (partial display area) of the imaging information 302 is located below the upper end of the imaging information display area, the display control unit 204a maintains the display position of the imaging information 302 (NO in step S401). This is equivalent to a case in which the radiation technician (imaging technician) has manually moved the display position of the prepared imaging information 302 to browse pre-imaging imaging information. Therefore, the display control unit 204a maintains the display position of the imaging information 302. That is, the display control unit 204a does not change the display position of the imaging information 302.

In step S402, the display control unit 204a performs display control so as to move (first movement) the display position of the prepared imaging information 302 to the middle (reference position) of the imaging information display area in accordance with the positional relationship determination result obtained in step S401.

In step S403, when the display position of the imaging information 302 is moved to the middle of the display area, imaging information displayed on the lower end of the imaging information display area can be partly omitted depending on the size of each partial display area for displaying each imaging information or the number of partial display areas. The display control unit 204a performs display control (display adjustment of lower end imaging information) so as to display all imaging information displayed on the lower end of the imaging information display area within the display area. A procedure for display control (display adjustment of lower end imaging information) by the display control unit 204a will be described with reference to FIGS. 5 and 6.

Figure 5:
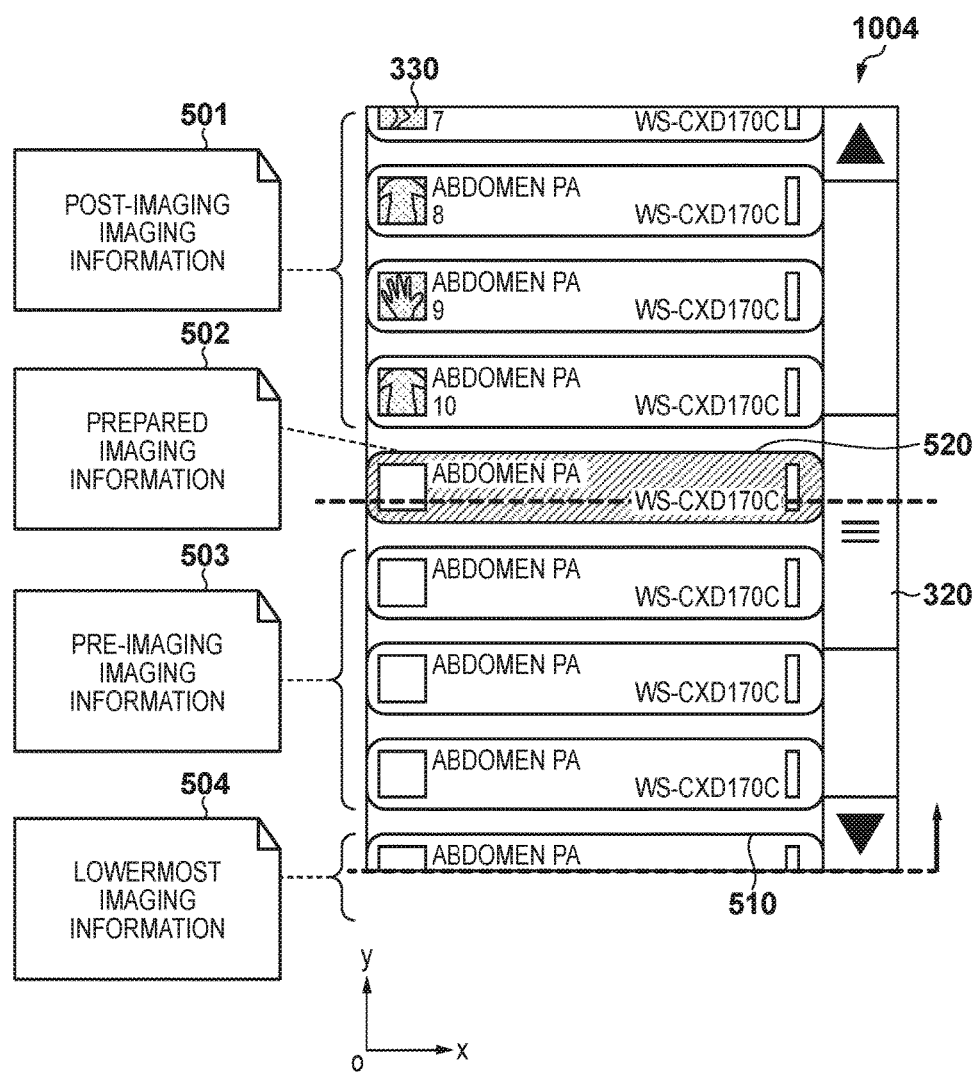
FIG. 5 is a view exemplarily showing display control performed by the display control unit.

FIG. 5 is a view showing the imaging information display area 1004 after the display position of the prepared imaging information 302 is moved to the middle of the imaging information display area. Like the imaging information 301 in FIG. 3, imaging information 501 is post-imaging information stored in the storage unit 203 in FIG. 2. Imaging information 502 is prepared imaging information which corresponds to the imaging information 302 in FIG. 3. The imaging information 502 is moved to the middle of the imaging information display area by the display control in step S402 in FIG. 4.

Imaging information 503 is imaging information corresponding to the imaging information 303 in FIG. 3 and is pre-imaging imaging information in the uncompleted state of preparation for imaging (unprepared imaging information) with respect to the sensor unit, which is to be used for imaging after the imaging information 502. Since the prepared imaging information 502 has moved to the middle of the imaging information display area, the unprepared imaging information 503 also moves in accordance with the movement of the imaging information 502. As a consequence, the unprepared imaging information 503 more than that in FIG. 3 is displayed in the imaging information display area. Imaging information 504 (lowermost imaging information) is imaging information displayed on the lower end in the display area. The imaging information 504 can be displayed with part of it being omitted depending on the size of a partial display area for displaying each imaging information or the number of partial display areas to be displayed.

Figure 6:
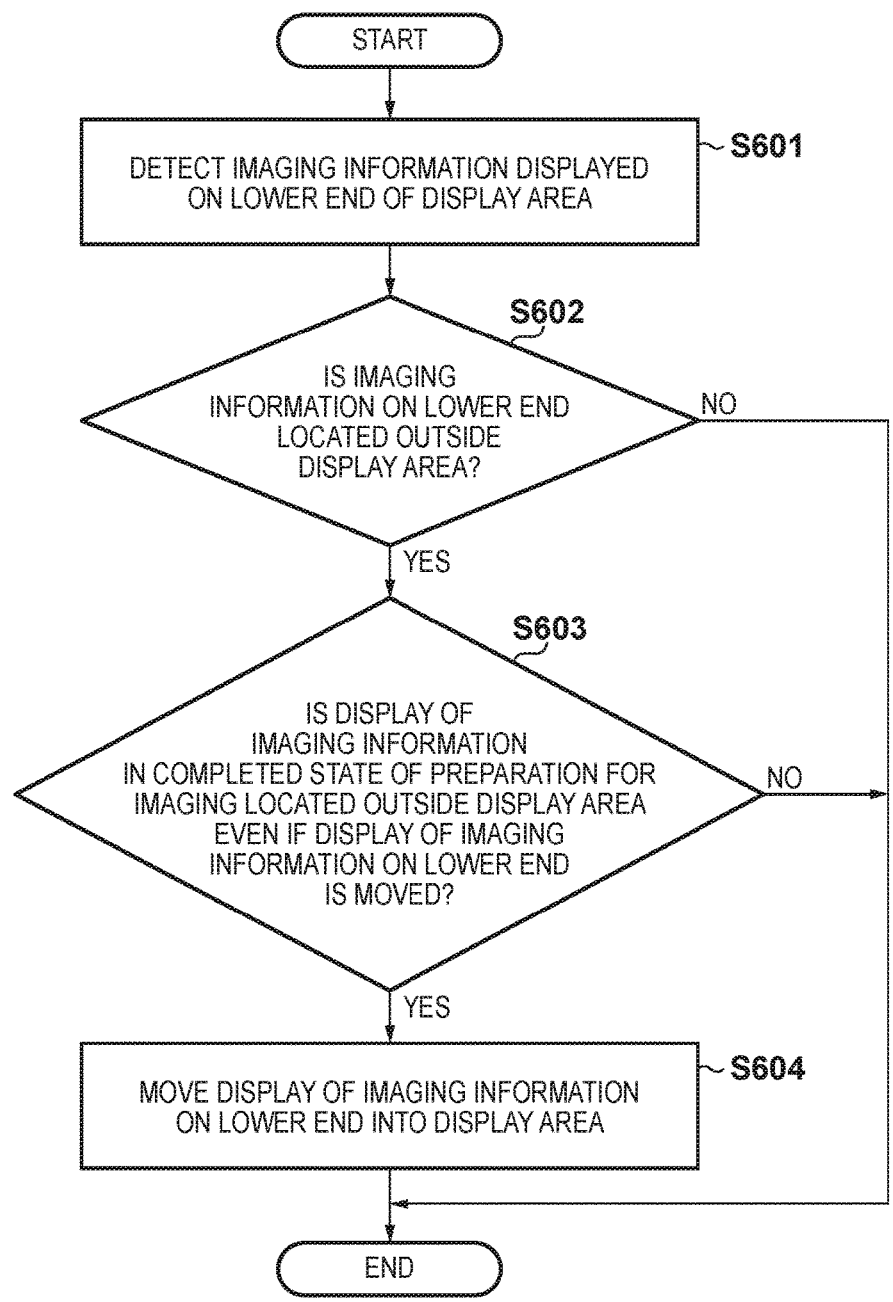
FIG. 6 is a flowchart for explaining a procedure for display adjustment on imaging information displayed near an end portion of an imaging information display area by the display control unit.

FIG. 6 is a flowchart for explaining a procedure for display control (display adjustment of imaging information displayed near an end portion of the imaging information display area) by the display control unit 204a. The display control unit 204a performs display control so as to display all the imaging information 504, which is displayed with part of it being omitted, without any discontinuity.

The display control unit 204a can set importances (priorities) on post-imaging information and pre-imaging imaging information. It is also possible to perform display control so as to switch between executing this processing when the importance (priority) of pre-imaging imaging information is higher than that of post-imaging information and not executing the processing when the importance (priority) of post-imaging imaging information is higher than that of pre-imaging information. Assume that although it is important to be able to check post-imaging information, a higher importance (priority) is placed on the display of pre-imaging imaging information. In this case, the following display control is performed to display pre-imaging imaging information on the lower end.

In step S601, the display control unit 204a detects imaging information displayed near an end portion (lower end) of the imaging information display area.

In step S602, the display control unit 204a determines whether a frame (partial display area) 510 on which the imaging information 504 on the lower end, which is detected in step S601, is displayed across the inside and outside of the imaging information display area 1004. The display control unit 204a compares the position of the upper end of the partial display area in which the imaging information on the lower end is displayed with the position of the lower end of the imaging information display area. In addition, the display control unit 204a compares the position of the lower end of the partial display area with the position of the lower end of the imaging information display area. These positions are based on a coordinate system for forming the display screen of the display unit 204b. When, therefore, changing the display position in the y direction in FIG. 5, the display control unit 204a uses the coordinates (position information) in the y direction for comparison processing.

If the comparison result indicates that the position of the upper end of the partial display area>the position of the lower end of the imaging information display area>the position of the lower end of the partial display area, the display control unit 204a determines that the partial display area in which the imaging information on the lower end is displayed is partially omitted (YES in step S602). The process then advances to step S603.

If it is determined in step S602 that the position of the upper end of the partial display area>the position of the lower end of the partial display area>the position of the lower end of the imaging information display area, the display control unit 204a determines that the partial display area in which the imaging information on the lower end is displayed is not omitted (NO in step S602), and all the partial display area is displayed in the display area. This processing is then terminated.

In addition, if the position of the lower end of the imaging information display area>the position of the upper end of the partial display area>the position of the lower end of the partial display area, the display control unit 204a determines that all the partial display area in which the imaging information on the lower end is displayed is located outside the imaging information display area, and is not displayed in an omitted state (NO in step S602). This processing is then terminated.

In step S603, the display control unit 204a determines whether the display of the prepared imaging information 502 is located outside the imaging information display area when all the partial display area in which the imaging information on the lower end is displayed moves (assuming that the moving amount is d1) so as to be displayed in the imaging information display area. The display control unit 204a obtains a distance d2 from the position of the upper end of a frame (partial display area) 520 in which the prepared imaging information 502 is displayed to the position of the upper end of the imaging information display area, which indicates a movement margin. The display control unit 204a compares the obtained distance d2 with a movement amount d1 of the imaging information on the lower end. If d2≥d1, the display control unit 204a determines that even if the imaging information on the lower end is moved, the display of the prepared imaging information 502 is not located outside the imaging information display area 1004 (YES in step S603). The process then advances to step S604.

If the determination in step S603 indicates that d1>d2, the display control unit 204*a* determines that if the imaging information on the lower end is moved, the display of the prepared imaging information 502 is located outside the imaging information display area 1004 (NO in step S603). The display control unit 204*a* then terminates this processing without moving the imaging information on the lower end.

In step S604, the display control unit 204*a* moves (second movement) the display of the imaging information on the lower end so as to display, in the imaging information display area 1004, an all partial display area 510 in which the imaging information on the lower end is displayed. Along with this movement, other pieces of imaging information also move. Display control by the display control unit 204*a* can display the prepared imaging information 502 in the imaging information display area and display pre-imaging imaging information following the imaging information 502 in the imaging information display area without any discontinuity. This makes it possible to save the effort and time taken by the imaging technician and provide display with excellent visibility.

Second Embodiment

Figure 7:
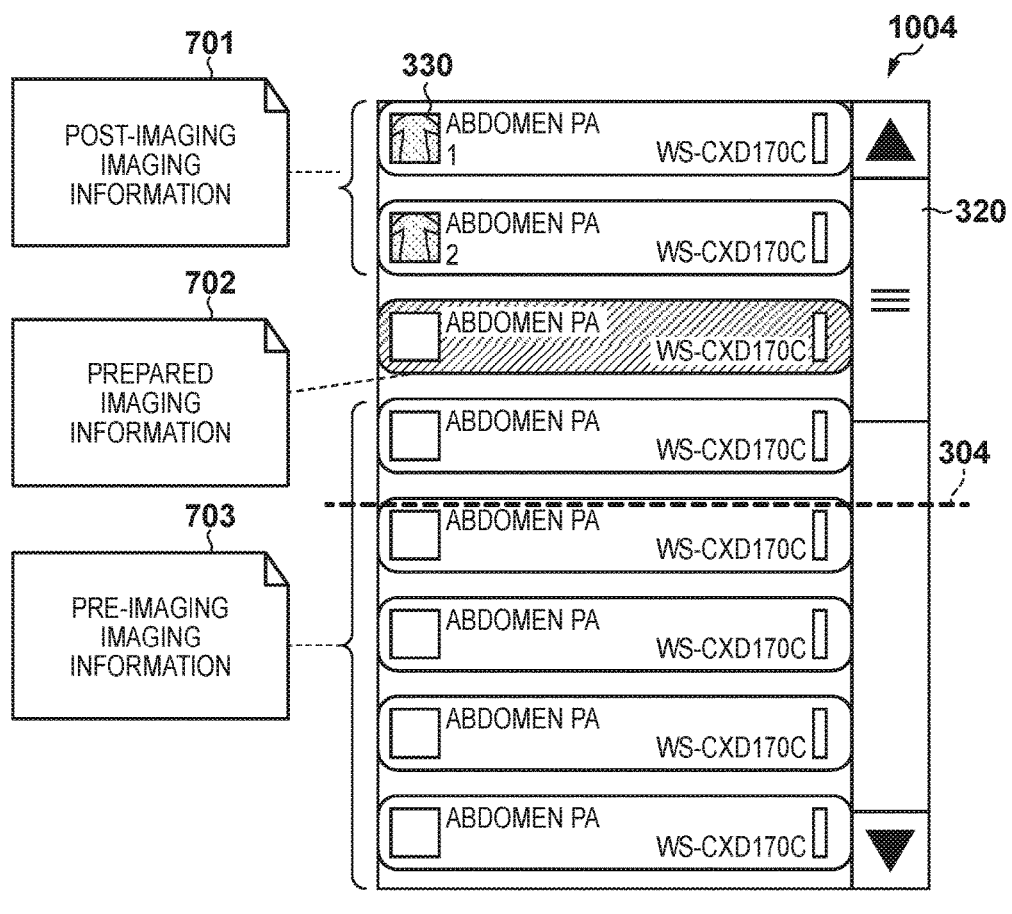
FIG. 7 is a view exemplarily showing display control performed by the display control unit.

The second embodiment will be described next when imaging is actually performed in accordance with an inspection order. The arrangement of an X-ray imaging apparatus and the arrangement of an imaging control unit according to this embodiment are the same as those shown in FIGS. 1 and 2. FIG. 7 is a view exemplarily showing the display of an imaging information display area 1004 when X-ray imaging is performed twice after the start of imaging in accordance with an inspection order. The first and second pieces of imaging information are post-imaging information 701. Third imaging information 702 indicates pre-imaging imaging information in the completed state of preparation for imaging. Imaging information 703 indicates pre-imaging imaging information in the uncompleted state of preparation for imaging. Since the display position of the imaging information 702 is located above the middle of the imaging information display area 1004, a display control unit 204*a* maintains the current display position without moving the display position of the imaging information 702. The display control unit 204*a* does not change the display position of the imaging information 702.

Figure 8:
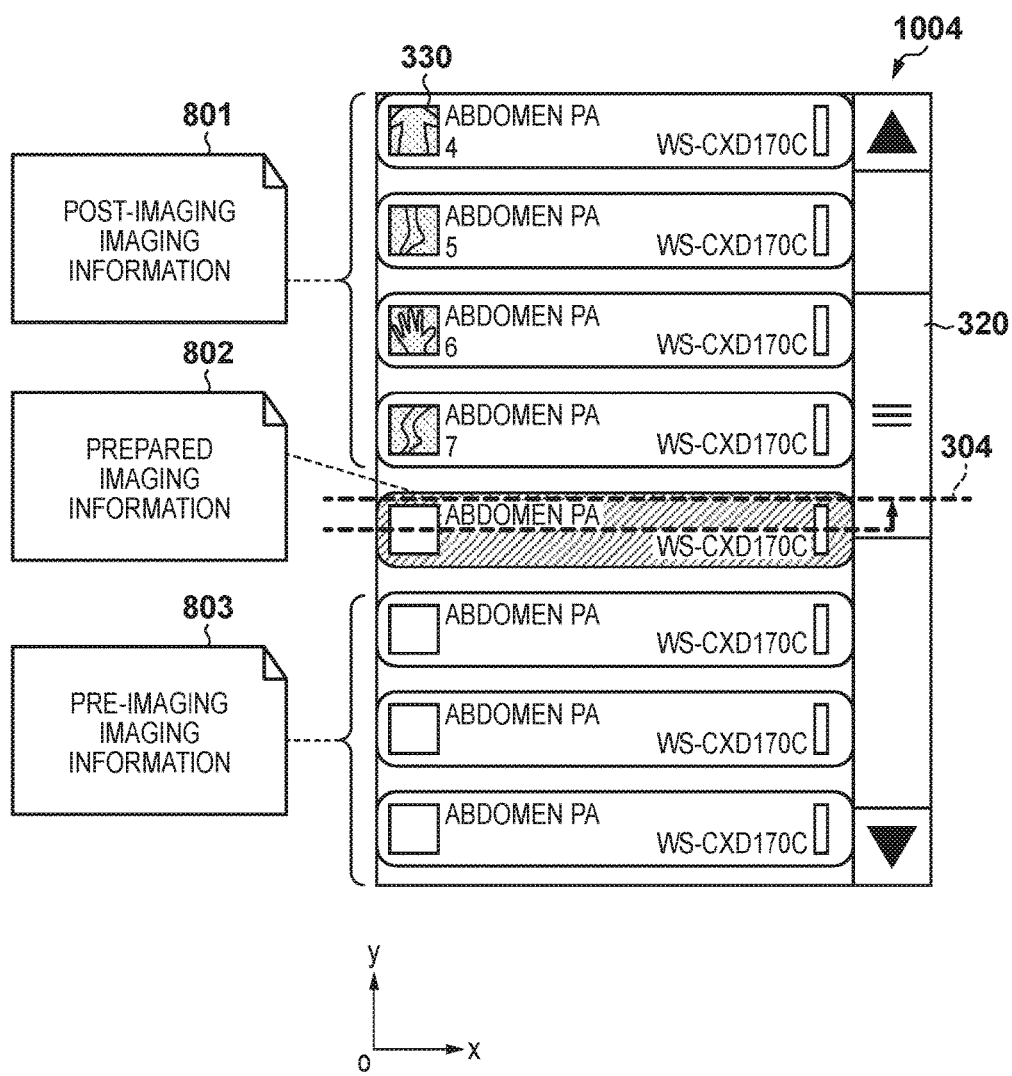
FIG. 8 is a view exemplarily showing display control performed by the display control unit.

FIG. 8 is a view exemplarily showing the imaging information display area 1004 when X-ray imaging is performed a plurality of times after the start of an inspection. Imaging information 801 is post-imaging information. Imaging information 802 is a pre-imaging imaging information in the completed state of preparation for imaging. The imaging information 802 is imaging information planned to be used for next imaging. Since the display position of the imaging information 802 is located below a reference position 304 in the imaging information display area, the display position is moved to the middle of the imaging information display area 1004 in accordance with display control in step S402 in FIG. 4. Along with this movement, pre-imaging imaging information 803 following the imaging information 802 also moves.

When the X-ray imaging progresses in this manner and the sensor unit 101 and the X-ray generation unit 102 have completed preparation for imaging, the display of imaging information planned to be used for next imaging is switched.

If the display position of the imaging information planned to be used for next imaging (prepared imaging information) is located below the reference position of the imaging information display area, the display control unit 204*a* performs display control so as to automatically change the display position of the prepared imaging information. This allows the radiation technician to perform imaging while checking both the post-imaging imaging information 801 and the unprepared imaging information 803 planned to be used for imaging without performing any special operation.

If imaging fails during an inspection, imaging information having undergone imaging again is added as post-imaging imaging information. In addition, when new imaging information is added upon, for example, editing of an inspection order, the added imaging information is added as pre-imaging imaging information. The added imaging information is subjected to the same display control as that described in the first embodiment. When the imaging preparation is complete, the display of the imaging information planned to be used for next imaging is switched. If the display position of the imaging information planned to be used for next imaging (prepared imaging information) is located below the reference position of the imaging information display area, the display control unit 204*a* performs display control so as to automatically change the display position of the prepared imaging information. This allows the radiation technician to perform imaging while checking both the post-imaging imaging information and the unprepared imaging information planned to be used for imaging without performing any special operation.

Figure 9:
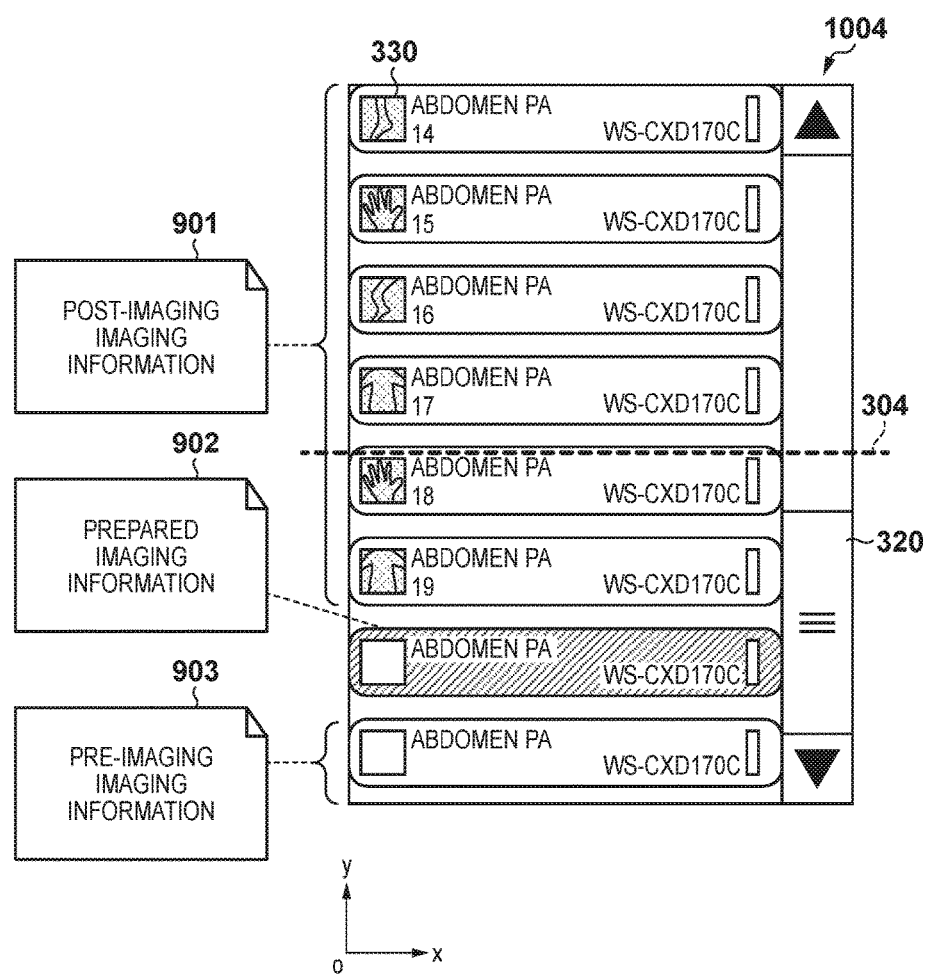
FIG. 9 is a view exemplarily showing display control performed by the display control unit.

FIG. 9 is a view exemplarily showing the imaging information display area 1004 at the last moment of an inspection. Imaging information 901 is post-imaging information. Imaging information 902 indicates pre-imaging imaging information in the completed state of preparation for imaging and is imaging information planned to be used for next imaging. The display position of the imaging information 902 planned to be used for next imaging is located below the reference position 304 (the middle in this case) in the imaging information display area. In this case, however, all the pre-imaging imaging information is displayed in the display area. For this reason, the display control unit 204*a* maintains the current display without moving the imaging information 902 planned to be used for next imaging and pre-imaging imaging information 903.

Third Embodiment

A display control unit 204*a* can collect and display pieces of imaging information displayed in the imaging information display area for each imaging region to be imaged. For example, the display control described in the first and second embodiment can be applied so as to collectively display pieces of imaging information concerning the same region such as a lung field region or abdominal region.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An imaging control apparatus for an X-ray imaging apparatus which performs X-ray imaging in accordance with a plurality of pieces of imaging information displayed in an information display area of a display unit, comprising:
   a display control unit configured to control a display position of prepared imaging information in a completed state of preparation for X-ray imaging and a display position of unprepared imaging information in an uncompleted state of preparation for X-ray imaging in accordance with a reference position set in the information display area; and
   a determination unit configured to determine whether the unprepared imaging information displayed in the information display area falls within the information display area by using the information display area and the display position of unprepared imaging information, wherein
   the display control unit changes the display position of prepared imaging information and the display position of unprepared imaging information so as to make the unprepared imaging information fall within the information display area when the unprepared imaging information does not fall within the information display area, and
   the display control unit does not change the display position of prepared imaging information and the display position of unprepared imaging information when the unprepared imaging information falls within the information display area.

2. The imaging control apparatus according to claim 1, wherein the display control unit displays imaging information which has become post-imaging imaging information upon execution of the X-ray imaging, the prepared imaging information, and the unprepared imaging information in the information display area.

3. The imaging control apparatus according to claim 1, wherein the display control unit controls the display position of prepared imaging information and the display position of unprepared imaging information in the information display area by comparing the display position of prepared imaging information with a reference position of the information display area.

4. The imaging control apparatus according to claim 1, wherein the display control unit changes the display position of prepared imaging information and the display position of unprepared imaging information so as to match the display position of the prepared imaging information with the reference position.

5. The imaging control apparatus according to claim 1, wherein the display control unit displays the prepared imaging information and the unprepared imaging information in the information display area when the prepared imaging information is not displayed in the information display area.

6. The imaging control apparatus according to claim 1, wherein when the display position of prepared imaging information and the display position of unprepared imaging information are changed, the determination unit determines whether prepared imaging information matched with the reference position is located outside an end portion of the information display area by using a position of the end portion in the information display area, the reference position, and a movement amount of display position based on the change.

7. The imaging control apparatus according to claim 6, wherein the display control unit does not change the display position of prepared imaging information and the display position of unprepared imaging information when the prepared imaging information falls outside the end portion of the information display area.

8. The imaging control apparatus according to claim 1, further comprising an operation input unit configured to change a display position of the information display data in accordance with an operation input, wherein
   the display control unit changes the display position of prepared imaging information and the display position of unprepared imaging information in the information display area in accordance with the operation input.

9. The imaging control apparatus according to claim 1, wherein the display control unit displays reduced display of an image obtained by the X-ray imaging in the information display area in combination with display of imaging information corresponding to the X-ray imaging.

10. The imaging control apparatus according to claim 1, further comprising an operation input unit which sets a reference position in the information display area.

11. A non-transitory computer readable storage medium storing a program for causing a computer to function as each unit of the imaging control apparatus according to claim 1.

12. An X-ray imaging apparatus which performs X-ray imaging, comprising:
   an X-ray generation unit configured to generate X-rays;
   a detection unit configured to detect the X-rays; and
   a display unit configured to display a plurality of pieces of imaging information for execution of X-ray imaging in an information display area and displaying an X-ray image based on the detection in an image display area,
   a display control unit configured to control a display position of prepared imaging information in a completed state of preparation for X-ray imaging and a display position of unprepared imaging information in an uncompleted state of preparation for X-ray imaging in accordance with a reference position set in the information display area; and
   a determination unit configured to determine whether the unprepared imaging information displayed in the information display area falls within the information display area by using the information display area and the display position of unprepared imaging information, wherein the display control unit changes the display position of prepared imaging information and the display position of unprepared imaging information so as to make the unprepared imaging information fall within the information display area when the unprepared imaging information does not fall within the information display area, and the display control unit does not change the display position of prepared imaging information and the display position of unprepared imaging information when the unprepared imaging information falls within the information display area.

13. An imaging control method for an X-ray imaging apparatus which performs X-ray imaging in accordance with a plurality of pieces of imaging information displayed in an information display area of a display unit, comprising:

a display control step of controlling a display position of prepared imaging information in a completed state of preparation for X-ray imaging and a display position of unprepared imaging information in an uncompleted state of preparation for X-ray imaging in accordance with a reference position set in the information display area; and a determination step of determining whether the unprepared imaging information displayed in the information display area falls within the information display area by using the information display area and the display position of unprepared imaging information, wherein the display control step changes the display position of prepared imaging information and the display position of unprepared imaging information so as to make the unprepared imaging information fall within the information display area when the unprepared imaging information does not fall within the information display area, and the display control step does not change the display position of prepared imaging information and the display position of unprepared imaging information when the unprepared imaging information falls within the information display area.

14. An imaging control apparatus for an X-ray imaging apparatus which performs X-ray imaging in accordance with a plurality of pieces of imaging information displayed in an information display area of a display unit, comprising:

a display control unit configured to control a display position of prepared imaging information in a completed state of preparation for X-ray imaging and a display position of unprepared imaging information in an uncompleted state of preparation for X-ray imaging in accordance with a reference position set in the information display area; and a determination unit configured to determine whether the unprepared imaging information displayed in the information display area falls within the information display area by using the information display area and the display position of unprepared imaging information, wherein the display control unit changes the display position of prepared imaging information and the display position of unprepared imaging information so as to make the unprepared imaging information fall within the information display area when the unprepared imaging information does not fall within the information display area, when the display position of prepared imaging information and the display position of unprepared imaging information are changed, the determination unit determines whether prepared imaging information matched with the reference position is located outside an end portion of the information display area by using a position of the end portion in the information display area, the reference position, and a movement amount of display position based on the change, and the display control unit does not change the display position of prepared imaging information and the display position of unprepared imaging information when the prepared imaging information falls outside the end portion of the information display area.

15. A non-transitory computer readable storage medium storing a program for causing a computer to function as each unit of the imaging control apparatus according to claim 14.

16. An imaging control method for an X-ray imaging apparatus which performs X-ray imaging in accordance with a plurality of pieces of imaging information displayed in an information display area of a display unit, comprising:

a display control step of controlling a display position of prepared imaging information in a completed state of preparation for X-ray imaging and a display position of unprepared imaging information in an uncompleted state of preparation for X-ray imaging in accordance with a reference position set in the information display area; and a determination step of determining whether the unprepared imaging information displayed in the information display area falls within the information display area by using the information display area and the display position of unprepared imaging information, wherein the display control step changes the display position of prepared imaging information and the display position of unprepared imaging information so as to make the unprepared imaging information fall within the information display area when the unprepared imaging information does not fall within the information display area, when the display position of prepared imaging information and the display position of unprepared imaging information are changed, the determination step determines whether prepared imaging information matched with the reference position is located outside an end portion of the information display area by using a position of the end portion in the information display area, the reference position, and a movement amount of display position based on the change, and the display control step does not change the display position of prepared imaging information and the display position of unprepared imaging information when the prepared imaging information falls outside the end portion of the information display area.

17. An imaging control apparatus for an X-ray imaging apparatus which performs X-ray imaging in accordance with a plurality of pieces of imaging information displayed in an information display area of a display unit, comprising:

a display control unit configured to control a display position of prepared imaging information in a completed state of preparation for X-ray imaging and a display position of unprepared imaging information in an uncompleted state of preparation for X-ray imaging in accordance with a reference position set in the information display area; and a determination unit configured to determine whether the unprepared imaging information displayed in the information display area falls within the information display area, wherein the display control unit changes the display position of prepared imaging information and the display position of unprepared imaging information so as to make the unprepared imaging information fall within the information display area in a case where the unprepared imaging information does not fall within the information display area, and the display control unit does not change the display position of prepared imaging information and the display position of unprepared imaging information in a case where the unprepared imaging information falls within the information display area.

18. A non-transitory computer readable storage medium storing a program for causing a computer to function as each unit of an imaging control apparatus according to claim 17.

19. An X-ray imaging apparatus which performs X-ray imaging, comprising:
an X-ray generation unit configured to generate X-rays;
a detection unit configured to detect the X-rays;
a display unit configured to display a plurality of pieces of imaging information for execution of X-ray imaging in an information display area and displaying an X-ray image based on the detection in an image display area:
a display control unit configured to control a display position of prepared imaging information in a completed state of preparation for X-ray imaging and a display position of unprepared imaging information in an uncompleted state of preparation for
X-ray imaging in accordance with a reference position set in the information display area; and
a determination unit configured to determine whether the unprepared imaging information displayed in the information display area falls within the information display area, wherein
the display control unit changes the display position of prepared imaging information and the display position of unprepared imaging information so as to make the unprepared imaging information fall within the information display area in a case where the unprepared imaging information does not fall within the information display area, and
the display control unit does not change the display position of prepared imaging information and the display position of unprepared imaging information in a case where the unprepared imaging information falls within the information display area.

20. An imaging control method for an X-ray imaging apparatus which performs X-ray imaging in accordance with a plurality of pieces of imaging information displayed in an information display area of a display unit, comprising:
a display control step of controlling a display position of prepared imaging information in a completed state of preparation for X-ray imaging and a display position of unprepared imaging information in an uncompleted state of preparation for X-ray imaging in accordance with a reference position set in the information display area; and
a determination step of determining whether the unprepared imaging information displayed in the information display area falls within the information display area, wherein
the display control step changes the display position of prepared imaging information and the display position of unprepared imaging information so as to make the unprepared imaging information fall within the information display area in a case where the unprepared imaging information does not fall within the information display area, and
the display control step does not change the display position of prepared imaging information and the display position of unprepared imaging information in a case where the unprepared imaging information falls within the information display area.

21. An imaging control apparatus for an X-ray imaging apparatus which performs X-ray imaging in accordance with a plurality of pieces of imaging information displayed in an information display area of a display unit, comprising:
a display control unit configured to control a display position of prepared imaging information in a completed state of preparation for X-ray imaging and a display position of unprepared imaging information in an uncompleted state of preparation for X-ray imaging in accordance with a reference position set in the information display area; and
a determination unit configured to determine whether the unprepared imaging information displayed in the information display area falls within the information display area, wherein
the display control unit changes the display position of prepared imaging information and the display position of unprepared imaging information so as to make the unprepared imaging information fall within the information display area in a case where the unprepared imaging information does not fall within the information display area,
in a case where the display position of prepared imaging information and the display position of unprepared imaging information are changed, the determination unit determines whether prepared imaging information matched with the reference position is located outside an end portion of the information display area, and
the display control unit does not change the display position of prepared imaging information and the display position of unprepared imaging information in a case where the prepared imaging information falls outside the end portion of the information display area.

22. A non-transitory computer readable storage medium storing a program for causing a computer to function as each unit of an imaging control apparatus according to claim 21.

23. An X-ray imaging apparatus which performs X-ray imaging, comprising:
an X-ray generation unit configured to generate X-rays;
a detection unit configured to detect the X-rays;
a display unit configured to display a plurality of pieces of imaging information for execution of X-ray imaging in an information display area and displaying an X-ray image based on the detection in an image display area;
a display control unit configured to control a display position of prepared imaging information in a completed state of preparation for X-ray imaging and a display position of unprepared imaging information in an uncompleted state of preparation for X-ray imaging in accordance with a reference position set in the information display area; and
a determination unit configured to determine whether the unprepared imaging information displayed in the information display area falls within the information display area, wherein
the display control unit changes the display position of prepared imaging information and the display position of unprepared imaging information so as to make the unprepared imaging information fall within the information display area in a case where the unprepared imaging information does not fall within the information display area, in a case where the display position of prepared imaging information and the display position of unprepared impinging information are changed, the determination unit determines whether prepared imaging information matched with the reference position is located outside an end portion of the information display area, and the display control unit does not change the display position of prepared imaging information and the display position of unprepared imaging information in a case where the prepared imaging information falls outside the end portion of the information display area.

24. An imaging control method for an X-ray imaging apparatus which performs X-ray imaging in accordance with a plurality of pieces of imaging information displayed in an information display area of a display unit, comprising:

a display control step of controlling a display position of prepared imaging information in a completed state of preparation for X-ray imaging and a display position of unprepared imaging information in an uncompleted state of preparation for X-ray imaging in accordance with a reference position set in the information display area; and a determination step of determining whether the unprepared imaging information displayed in the information display area falls within the information display area, wherein the display control step changes the display position of prepared imaging information and the display position of unprepared imaging information so as to make the unprepared imaging information fall within the information display area in a case where the unprepared imaging information does not fall within the information display area, in a case where the display position of prepared imaging information and the display position of unprepared imaging information are changed, the determination step determines whether prepared imaging information matched with the reference position is located outside an end portion of the information display area, and the display control step does not change the display position of prepared imaging information and the display position of unprepared imaging information in a case where the prepared imaging information falls outside the end portion of the information display area.

* * * * *